United States Patent
Wu (10) Patent No.: US 10,890,792 B2
(45) Date of Patent: Jan. 12, 2021

(54) AUTO DARKENING FILTER CAPABLE OF ACHIEVING HIGH LIGHT-SHIELDING NUMBER

(71) Applicant: Tecmen Electronics Co., Ltd., Jiangsu (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 93 days.

(21) Appl. No.: 16/315,454

(22) PCT Filed: Jan. 16, 2017

(86) PCT No.: PCT/CN2017/071245
§ 371 (c)(1),
(2) Date: Jan. 4, 2019

(87) PCT Pub. No.: WO2018/072355
PCT Pub. Date: Apr. 26, 2018

(65) Prior Publication Data
US 2019/0310503 A1  Oct. 10, 2019

(30) Foreign Application Priority Data

Oct. 20, 2016  (CN) .......................... 2016 1 0914734

(51) Int. Cl.
*G02F 1/133* (2006.01)
*A61F 9/06* (2006.01)
(Continued)

(52) U.S. Cl.
CPC ............ *G02F 1/13318* (2013.01); *A61F 9/06* (2013.01); *A61F 9/067* (2013.01); *G02F 1/13* (2013.01);
(Continued)

(58) Field of Classification Search
CPC ........ G02F 1/13318; G02F 1/13; G02F 1/133; G02F 1/133514; A61F 9/06; A61F 9/067
See application file for complete search history.

(56) References Cited

U.S. PATENT DOCUMENTS 5,793,449 A     8/1998  Lagerwall
2010/0265421 A1*  10/2010  Sundell ................ G02F 1/1313
                                                      349/14
(Continued)

FOREIGN PATENT DOCUMENTS

CN              2177464 Y       9/1994
CN            102217988 A      10/2011
(Continued)

*Primary Examiner* — Nathanael R Briggs (57) ABSTRACT

An auto darkening filter, comprising: a first positive liquid crystal (LCD1) a second positive liquid crystal (LCD2); a first liquid crystal control circuit (A) configured to control the first positive liquid crystal (LCD1) and the second positive liquid crystal (LCD2) based on a received control signal; a negative-phase liquid crystal (LCD3) provided between the first positive liquid crystal (LCD1) and the second positive liquid crystal (LCD2); a second liquid crystal control circuit (B) configured to control the negative-phase liquid crystal (LCD3) based on a received control signal; a UV/IR filter configured to filter a welding arc; a light control circuit configured to detect the welding arc, generate a corresponding control signal based on the detected intensity of the welding arc, and output the corresponding control signal to a main control circuit.

18 Claims, 4 Drawing Sheets

(51) Int. Cl.
  *G02F 1/1335* (2006.01)
  *G02F 1/13* (2006.01)
(52) U.S. Cl.
  CPC ........ *G02F 1/133* (2013.01); *G02F 1/133514* (2013.01)

(56) References Cited

U.S. PATENT DOCUMENTS

| | | | |
|---|---|---|---|
| 2014/0104551 A1* | 4/2014 | Cui | G02F 1/13363 349/117 |
| 2015/0001378 A1 | 1/2015 | Magnusson et al. | |
| 2016/0262467 A1* | 9/2016 | Magnusson | G02F 1/133305 |

FOREIGN PATENT DOCUMENTS

| | | | |
|---|---|---|---|
| CN | 104115041 A | 10/2014 | |
| CN | 104854485 A | 8/2015 | |
| CN | 206096678 U | 4/2017 | |
| KR | 10-2016-0004080 A | 1/2016 | |

* cited by examiner

AUTO DARKENING FILTER CAPABLE OF ACHIEVING HIGH LIGHT-SHIELDING NUMBER

CROSS-REFERENCE TO RELATED APPLICATIONS

This application is a 371 National Stage of International Application No. PCT/CN2017/071245 filed Jan. 16, 2017, which claims priority to Chinese Patent Application No. 201610914734.X filed Oct. 20, 2016, the disclosures of which are herein incorporated by reference in their entirety.

BACKGROUND

1. Field

The present invention relates to the field of optoelectronic technology, in particular to an auto darkening filter, which can be used for protecting a user's eyes in a strong light environment.

2. Description of Related Art

Currently, an auto darkening filter (ADF) in the prior art is composed of a liquid crystal, a control circuit, a solar panel/battery, a light sensor, and an ultraviolet and infrared filter. The liquid crystal in the auto-darkening filter typically contains two pieces of positive liquid crystals. In a strong light environment, for example, when a welding arc occurs, the light sensor receives the welding arc and notifies the control circuit of it. The control circuit outputs a square wave signal to the two pieces of positive liquid crystals, thereby instantaneously triggering the liquid crystal in the auto darkening filter and causing the liquid crystal to darken. The ultraviolet rays and infrared rays in the welding arc are reflected off; appropriate visible light is projected to the eye ground of the user; and the light transmission is reduced to an appropriate extent. At present, the light-shielding number of the auto darkening filter is generally in the range of No. 5 to 13; and by adjusting the voltage amplitude of the square wave signal, the light-shielding number may be changed in the range of No. 5 to 13.

However, it is difficult for the auto darkening filter of prior art to achieve higher light-shielding number and to enable the liquid crystal assembly to exhibit higher darkness effect. This results in that the eye protection effect of the auto darkening filter is not optimal and its power consumption is not reduced to the minimum.

SUMMARY

In order to solve the above technical problem, the present invention provides an auto darkening filter, comprising: a first positive liquid crystal and a second positive liquid crystal; a first liquid crystal control circuit configured to control the first positive liquid crystal and the second positive liquid crystal based on a received control signal; a negative-phase liquid crystal disposed between the first positive liquid crystal and the second positive liquid crystal; a second liquid crystal control circuit configured to control the negative-phase liquid crystal based on a received control signal; UV/IR (ultraviolet/infrared) filter configured to filter the welding arc; a light control circuit configured to detect a light intensity of the welding arc, generate a corresponding control signal based on the detected light intensity of the welding arc and output the control signal to a main control circuit; and the main control circuit connected with the light control circuit, the first liquid crystal control circuit and the second liquid crystal control circuit respectively, and configured to output liquid crystal control signals to the first liquid crystal control circuit and the second liquid crystal control circuit.

According to an embodiment of the present invention, the auto darkening filter further comprises: a darkness setting unit connected to the main control circuit, and configured to set a light-shielding number of the auto darkening filter; the main control circuit is configured to generate a corresponding liquid crystal control signal based on the light-shielding number set by the darkness setting unit, to control the first positive liquid crystal, the second positive liquid crystal, and the negative phase liquid crystal, and to enable the auto darkening filter to exhibit the set light-shielding darkness.

According to an embodiment of the present invention, when the auto darkening filter is in a standby state and the light-shielding number is set as No. 2.5 to No. 4, under the control of the main control circuit, the first liquid crystal control circuit provides, to the first positive liquid crystal and the second positive liquid crystal, an operating voltage of 0v; and the control signal provided by the second liquid crystal control circuit to the negative-phase liquid crystal is a square wave or DC voltage with an operating voltage of 2.5v to 15v and a frequency of 0.05 Hz to 20 Hz.

According to an embodiment of the present invention, when the light-shielding number is set as No. 5 to No. 15, under the control of the main control circuit, a control signal provided by the first liquid crystal control circuit to the first positive liquid crystal and the second positive liquid crystal is a square wave with an operating voltage of 1.5V to 8v and a frequency of 10 Hz to 60 Hz; and a control signal provided by the second liquid crystal control circuit to the negative-phase liquid crystal is a square wave or DC voltage with an operating voltage of 2.5v to 15v and a frequency of 0.05 Hz to 20 Hz.

According to an embodiment of the present invention, the first liquid crystal control circuit provides, to the first positive liquid crystal and the second positive liquid crystal, the square wave with a preferable operating voltage of 3v to 8v, to achieve light-shielding number s of 14, 15 or higher.

According to an embodiment of the present invention, when the light sensor in the light control circuit detects an end of welding operation, the main control circuit outputs, to the first liquid crystal control circuit and the second liquid crystal control circuit, a darkness gradient control signal for gradually changing the light-shielding darkness of the auto darkening filter from high to low.

According to an embodiment of the present invention, the auto darkening filter further comprises at least one of the following units connected to the main control circuit: a delay setting unit configured to set a filter delay of the auto darkening filter; and a sensitivity setting unit configured to set a filter sensitivity of the auto darkening filter.

According to an embodiment of the present invention, the first positive liquid crystal and the second positive liquid crystal are positive normal-phase liquid crystals; and the negative-phase liquid crystal is a positive negative-phase liquid crystal.

The present invention further provides a welding mask assembly, which comprises the auto darkening filter as stated above.

The auto darkening filter and welding mask of the present invention can achieve higher light-shielding numbers than prior arts, thereby optimizing the eye protection effect and minimizing its power consumption.

Embodiments of the present invention will be described in detail below with reference to the accompanying drawings.

DETAILED DESCRIPTION

Figure 1:
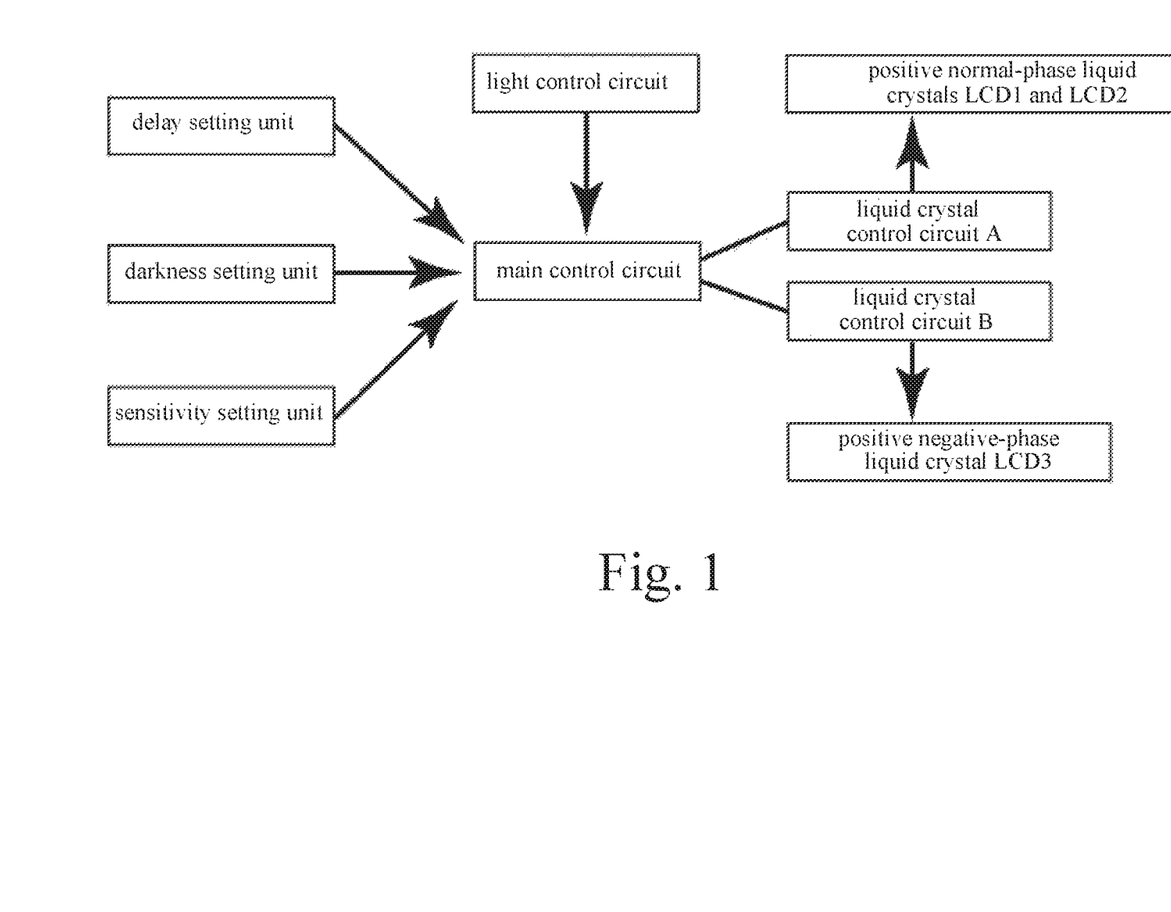
FIG. 1 shows a block diagram of a circuit configuration of an embodiment of an auto darkening filter of the present invention.

FIG. 1 shows the circuit configuration of an embodiment of the auto darkening filter of the present invention. In this embodiment, the circuit portion of the auto darkening filter includes a main control circuit, a light control circuit, a liquid crystal control circuit A, and a liquid crystal control circuit B. The main control circuit is connected with the light control circuit, the liquid crystal control circuit A and the liquid crystal control circuit B respectively. The main control circuit also receives a filtering delay control parameter, a filtering darkness control parameter, and a filtering sensitivity control parameter that are preset or input (as shown on the left side of FIG. 1). The liquid crystal control circuit A is configured to control the positive normal-phase liquid crystals LCD1 and LCD2; and the liquid crystal control circuit B is configured to control the positive negative-phase liquid crystal LCD3.

Figure 2:
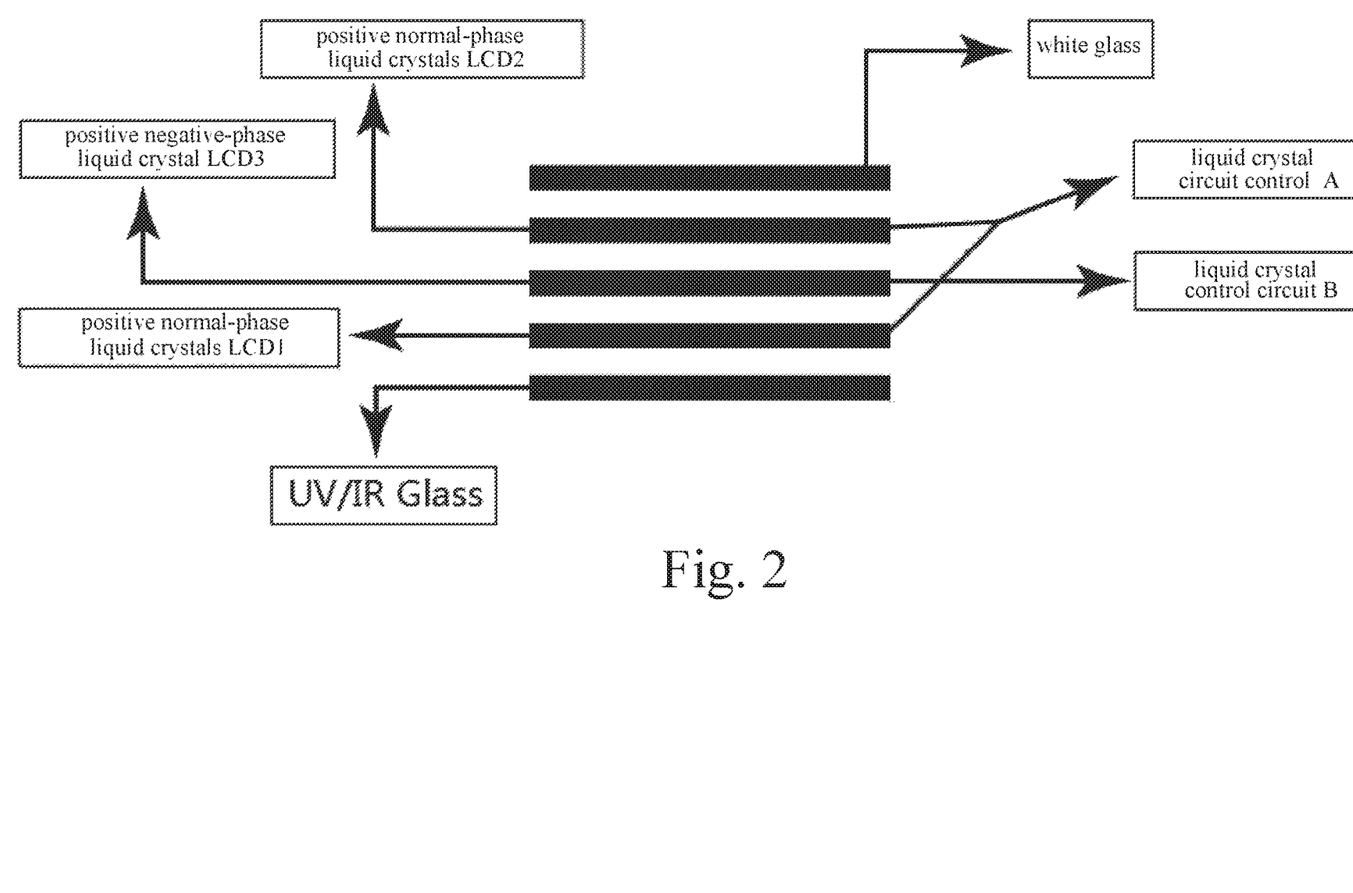
FIG. 2 shows a schematic view of relative position relationship of liquid crystals in the embodiment of the auto darkening filter of the present invention.

FIG. 2 shows the relative positional relationship of liquid crystals in the embodiment of the auto darkening filter of the present invention. As shown in FIG. 2, optical components (i.e., five black strips in the middle of FIG. 2) includes: an ultraviolet/infrared filter (UV/IR Glass), a positive normal-phase liquid crystal LCD1, a positive negative-phase liquid crystal LCD3, a positive normal-phase liquid crystal LCD2 and a white glass with protective function, in order from bottom to top. It is assumed here that the welding arc is incident from bottom to top. The liquid crystal control circuit A is connected with and controls the positive normal-phase liquid crystals LCD1 and LCD2; and the liquid crystal control circuit B is connected with and controls the positive negative-phase liquid crystal LCD3.

This embodiment utilizes two pieces of positive normal-phase liquid crystals and one piece of positive negative-phase liquid crystal. The phase angle of the positive negative-phase liquid crystal is opposite to phase angles of the two pieces of positive normal-phase liquid crystals. In order to cooperate with the operation mode of the three pieces of liquid crystals, two pieces of positive normal-phase liquid crystals and one piece of positive negative-phase liquid crystal are connected to two different liquid crystal control circuits. The two liquid crystal control circuits adjust operating voltages of two pieces of positive normal-phase liquid crystals and one piece of positive negative-phase liquid crystal, so that a light-shielding number of 14, 15 or higher can be achieved. By adjusting the operating voltage of the positive negative-phase liquid crystal as blackness compensation, on the basis of achieving the light-shielding number of 14, 15 or higher, the light-shielding darkness of the auto darkening filter on standby can be reduced to 2.5 to 4.0; and users can have more clear and bright observation of the standby state to ensure better welding preparation.

In an embodiment of the present invention, LCD1 and LCD2 are positive normal-phase liquid crystals; and LCD3 is a positive negative-phase liquid crystal. No polarizer is provided on glass surfaces on both sides of the liquid crystal of LCD3; and a pre-tilt angle of the liquid crystal molecules is of negative-phase collocation with a polarizer on the glass surface in contact with LCD1 and LCD2.

When the three pieces of liquid crystals are not powered, a light enters from LCD1; then, since LCD3 is of negative collocation with LCD1, the light cannot completely enter LCD2 through LCD3, and the combination of the three pieces of liquid crystals appears opaque. A large or small darkness can be achieved by adjusting the pre-tilt angle of the liquid crystal of LCD3. When LCD1 and LCD2 are not powered and LCD3 is powered up, liquid crystal molecules of LCD3 rotate and form a normal-phase collocation with LCD1 and LCD2, thereby the combination of the three pieces of liquid crystals appears to be light transmissible.

When a welding arc occurs, a light sensor included in the light control circuit detects the welding arc; and after being processed by an operational amplifier, the detected signal is sent by the light control circuit to the main control circuit. The main control circuit can accordingly set the light-shielding darkness (corresponding to the light-shielding number) of the automatic darkening filter based on the detected intensity of the welding arc; or the light-shielding darkness may be set or input by the user. The main control circuit may include a microprogrammed control unit (MCU). During operation, the MCU reads a delay control parameter, a darkness control parameter and a sensitivity control parameter set or input by a user, and outputs corresponding control signals to the liquid crystal control circuits A and B to control LCD1, LCD2 and LCD3, to enable the welding arc to exhibit the set darkness after passing through these liquid crystals, in order to protect the user's eyes from injury.

When the auto darkening filter is in standby state, or the light-shielding number of the auto darkening filter is set to be DIN 2.5-DIN 4 (DIN represents the unit of sensitivity of the German Industrial Standard photosensitive sheet), the main control circuit passes applies a voltage of 0V to LCD1 and LCD2 through the liquid crystal control circuit A; the operating voltage of the liquid crystal control circuit B is a square wave or DC voltage with a low frequency of 0.05-20 Hz and a voltage amplitude of 2.5V-15V.

When the darkness parameter is set between No. 5-13, the signal applied to the liquid crystal control circuit A is a square wave with a frequency of 10-60 Hz and a voltage amplitude of 1.5V-8V, and the signal applied to the liquid crystal control circuit B is a square wave or DC voltage with a low frequency of 0.05-20 Hz and a voltage amplitude of 2.5V-15V.

When the darkness parameter is set to be a light-shielding number of 14, 15 or higher, a square wave of 3V-8V is applied to the two pieces of positive normal-phase liquid crystals LCD1 and LCD2; at this time, by adjusting the operating voltage outputted by the liquid crystal control circuit B to the positive negative-phase liquid crystal LCD3, the darkness of No. 14, 15 or higher can be achieved, and the power consumption of the auto darkening filter can also be saved.

When the welding work is finished, the welding arc disappears. The main control circuit adjusts the operating voltage on the positive negative-phase liquid crystal by outputting a control signal to the liquid crystal control circuit B, to gradually change the light-shielding number of the auto darkening filter from No. 14, 15 or higher to, finally, a light-shielding number at a bright state of inoperation, so as to ensure that user's eyes can adapt to the process of darkness changing, and to improve the comfort level of user's eyes. For example, when the welding work is finished, the operating voltages applied to LCD1 and LCD2 are released first; LCD3 is set in advance so that the light-shielding darkness of the auto darkening filter is No. 5-7; and then the liquid crystal control circuit B outputs a square wave or a level to LCD3, to gradually reduce the light-shielding darkness of the auto darkening filter to, for example, No. 2.5 to 4, thereby realizing a darkness gradation from high to low.

In an embodiment of the present invention, the positive liquid crystals LCD1 and LCD2 may be positive normal-phase liquid crystals, and the negative-phase liquid crystal LCD3 may be a positive negative-phase liquid crystal.

Figure 3:
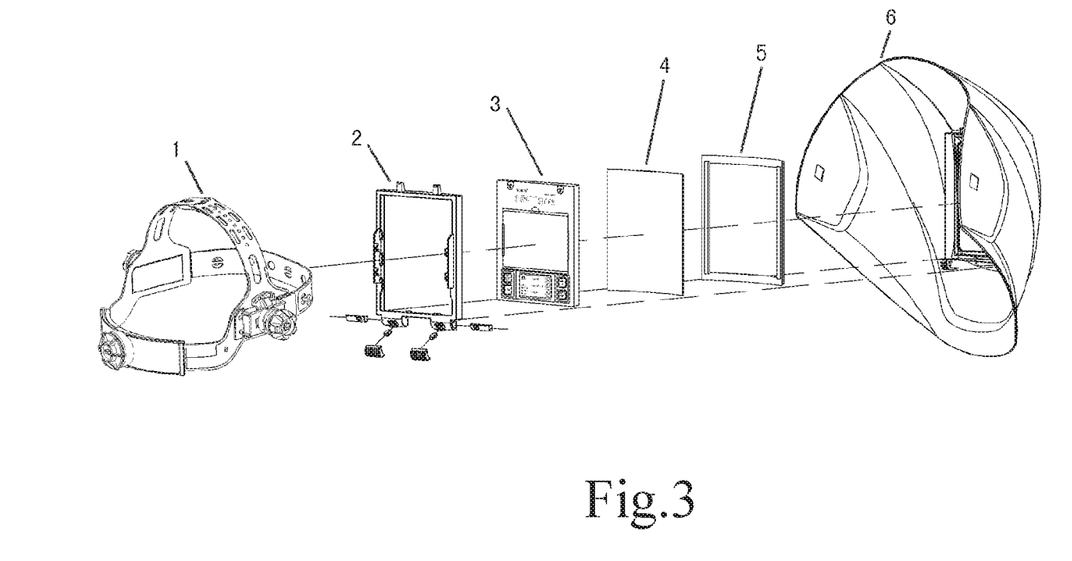
FIG. 3 shows a structure schematic view of an embodiment of the welding mask assembly of the present invention.

FIG. 3 shows the structure of an embodiment of a welding mask assembly of the present invention. The welding mask assembly includes: an adjustable headband (1) for a user to wear, a filter holder (2) for supporting an auto darkening filter, an auto darkening filter (3), a front protective sheet (4) for protecting the auto darkening filter, a sealing member (5) and a welding mask (6).

Figure 4:
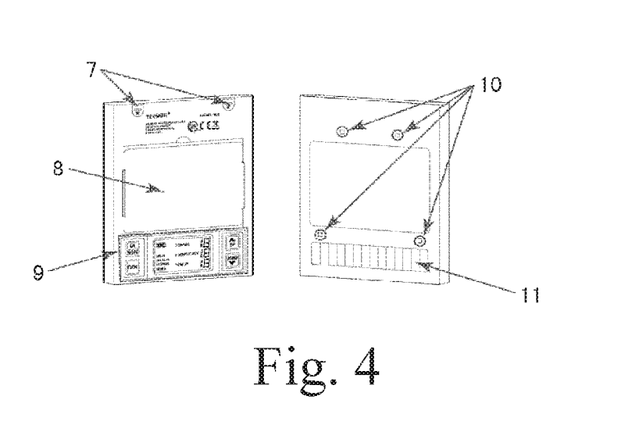
FIG. 4 shows a schematic view of a front side and a rear side of the auto darkening filter in the embodiment shown in FIG. 3.

The left and right parts in FIG. 4 respectively show a rear side and a front side of the auto darkening filter (3) as shown in FIG. 3. On the rear side shown in the left part of FIG. 4, a battery case (7) for accommodating a battery, a liquid crystal panel (8) and a function operating area (9) are arranged. On the front side shown in the right part of FIG. 4, a plurality of welding arc sensors (10) for detecting the welding arc and a solar panel (11) provided for solar cells are arranged.

In an embodiment of the present invention, the auto darkening filter (3) may include a plurality of function buttons and a digital display which are disposed in the function operating area (9), and corresponding circuit units including a delay setting unit, a darkness setting unit and a sensitivity setting unit which are used for setting or inputting the delay control parameter, the darkness control parameter and the sensitivity control parameter, respectively.

Figure 5:
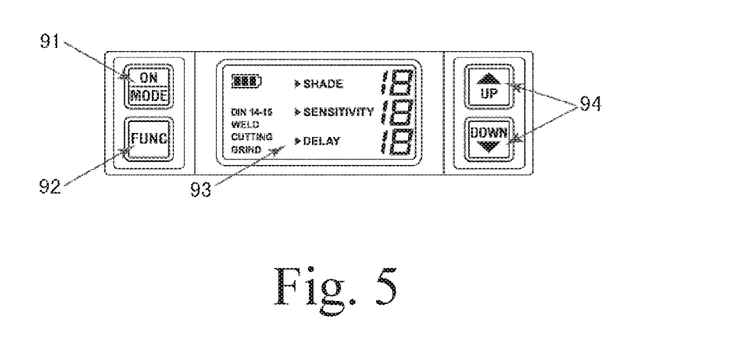
FIG. 5 shows a schematic view of a functional operation area on the rear side of the auto darkening filter shown in FIG. 4.

As shown in FIG. 5, the function operating area (9) contains a power-on key "ON", a mode switching key "MODE" (91), a function switching key "FUNC" (92), a digital display (93) and function digital adjustment keys "UP" and "DOWN" (94). The power-on button "ON" is configured to turn on the auto darkening filter; and the mode switching key "MODE" may be used for switching among, e.g., four modes, including "darkness No. 14-15 (DIN 14-15)", "welding (WELD)", "cutting (CUTTING)" and "grinding (GRIND)", to set operating modes of the auto darkening filter to achieve corresponding different light-shielding darkness. The function switching key "FUNC" (92) is configured to switch functions of setting three parameters, including darkness (SHADE), sensitivity (SENSITIVITY) and time delay (DELAY). The digital display (93) may display these three parameters, the set above modes and the battery level. The function digital adjustment keys are configured to increase or decrease the number of parameters listed on the right side of the digital display (93) by pressing the keys "UP" and "DOWN" (94) when a function option is selected.

The invention claimed is:

1. An auto darkening filter, comprising:
a first positive liquid crystal and a second positive liquid crystal;
a first liquid crystal control circuit configured to control the first positive liquid crystal and the second positive liquid crystal based on a first control signal;
a negative-phase liquid crystal disposed between the first positive liquid crystal and the second positive liquid crystal;
a second liquid crystal control circuit configured to control the negative-phase liquid crystal based on a second control signal;
UV/IR filter configured to filter a welding arc;
a light control circuit configured to detect a light intensity of the welding arc, generate a corresponding control signal based on the detected light intensity of the welding arc and output the control signal to a main control circuit; and
the main control circuit connected with the light control circuit, the first liquid crystal control circuit and the second liquid crystal control circuit respectively, and configured to output the first and second control signals to the first liquid crystal control circuit and the second liquid crystal control circuit, respectively, to control the first liquid crystal control circuit and the second liquid crystal control circuit to output different voltages to (i) the first and second positive liquid crystals and (ii) the negative-phase liquid crystal, respectively.

2. The auto darkening filter according to claim 1, further comprising:
a darkness setting unit connected to the main control circuit and configured to set a light-shielding number of the auto darkening filter;
wherein the main control circuit is configured to:
generate the first and second control signals to control the first liquid crystal control circuit and the second liquid crystal control circuit, respectively, to output the different voltages to (i) the first and second positive liquid crystals and (ii) the negative-phase liquid crystal, respectively, based on the light-shielding number set by the darkness setting unit to enable the auto darkening filter to exhibit darkness set by the light-shielding number.

3. The auto darkening filter according to claim 2, wherein the main control circuit is configured to:
detect that the light-shielding number is set as No. 2.5 to No. 4,
control the first liquid crystal control circuit to provide an operating voltage of 0V to the first positive liquid crystal and the second positive liquid crystal; and
control the second liquid crystal control circuit to provide to the negative-phase liquid crystal a square wave or DC voltage with an operating voltage of 2.5v to 15v and a frequency of 0.05 Hz to 20 Hz.

4. The auto darkening filter according to claim 2, wherein the main control circuit is configured to:
detect that the light-shielding number is set as No. 5 to No. 15,
control the first liquid crystal control circuit to provide to the first positive liquid crystal and the second positive liquid crystal a square wave with an operating voltage of 1.5V to 8V and a frequency of 10 Hz to 60 Hz; and
control the second liquid crystal control circuit to provide to the negative-phase liquid crystal a square wave or DC voltage with an operating voltage of 2.5V to 15V and a frequency of 0.05 Hz to 20 Hz.

5. The auto darkening filter according to claim 4, wherein the first liquid crystal control circuit provides, to the first positive liquid crystal and the second positive liquid crystal, the square wave with an operating voltage of 3v to 8v.

6. The auto darkening filter according to claim 1, wherein when a light sensor in the light control circuit detects an end of welding operation, the main control circuit is configured to:
control the first liquid crystal control circuit to stop outputting the first control signal to the first positive liquid crystal and the second positive liquid crystal; and
control the second liquid crystal control circuit to output a darkness gradient control signal to the negative-phase liquid crystal for gradually changing a light-shielding number of the auto darkening filter from high to low.

7. The auto darkening filter according to claim 1, further comprising at least one of:
a delay setting unit configured to set a filter delay of the auto darkening filter; or
a sensitivity setting unit configured to set a filter sensitivity of the auto darkening filter,
operably to the main control circuit.

8. The auto darkening filter according to claim 1, wherein the first positive liquid crystal and the second positive liquid crystal are positive normal-phase liquid crystals; and the negative-phase liquid crystal is a positive negative-phase liquid crystal.

9. A welding mask assembly, comprising:
an auto darkening filter comprising:
a first positive liquid crystal and a second positive liquid crystal;
a first liquid crystal control circuit configured to control the first positive liquid crystal and the second positive liquid crystal based on a first control signal;
a negative-phase liquid crystal disposed between the first positive liquid crystal and the second positive liquid crystal;
a second liquid crystal control circuit configured to control the negative-phase liquid crystal based on a second control signal;
UV/IR filter configured to filter a welding arc;
a light control circuit configured to detect a light intensity of the welding arc, generate a corresponding control signal based on the detected light intensity of the welding arc and output the control signal to a main control circuit; and
the main control circuit connected with the light control circuit, the first liquid crystal control circuit and the second liquid crystal control circuit respectively, and configured to output the first and second control signals to the first liquid crystal control circuit and the second liquid crystal control circuit, respectively, to control the first liquid crystal control circuit and the second liquid crystal control circuit to output different voltages to (i) the first and second positive liquid crystals and (ii) the negative-phase liquid crystal, respectively.

10. The welding mask assembly according to claim 9, wherein the auto darkening filter further comprises:
a darkness setting unit connected to the main control circuit and configured to set a light-shielding number of the auto darkening filter;
wherein the main control circuit is configured to:
generate the first and second control signals to control the first liquid crystal control circuit and the second liquid crystal control circuit, respectively, to output the different voltages to (i) the first and second positive liquid crystals and (ii) the negative-phase liquid crystal, respectively, based on the light-shielding number set by the darkness setting unit to enable the auto darkening filter to exhibit darkness set by the light-shielding number.

11. The welding mask assembly according to claim 10, wherein the main control circuit is configured to:
detect that the light-shielding number is set as No. 2.5 to No. 4,
control the first liquid crystal control circuit to provide an operating voltage of 0v to the first positive liquid crystal and the second positive liquid crystal; and
control the second liquid crystal control circuit to provide to the negative-phase liquid crystal a square wave or DC voltage with an operating voltage of 2.5v to 15v and a frequency of 0.05 Hz to 20 Hz.

12. The welding mask assembly according to claim 10, wherein the main control circuit is configured to:
detect that the light-shielding number is set as No. 5 to No. 15,
control the first liquid crystal control circuit to provide to the first positive liquid crystal and the second positive liquid crystal a square wave with an operating voltage of 1.5V to 8v and a frequency of 10 Hz to 60 Hz; and
control the second liquid crystal control circuit to provide to the negative-phase liquid crystal a square wave or DC voltage with an operating voltage of 2.5v to 15v and a frequency of 0.05 Hz to 20 Hz.

13. The welding mask assembly according to claim 12, wherein the first liquid crystal control circuit provides, to the first positive liquid crystal and the second positive liquid crystal, the square wave with an operating voltage of 3v to 8v.

14. The welding mask assembly according to claim 9, wherein when a light sensor in the light control circuit detects an end of welding operation, the main control circuit is configured to:
control the first liquid crystal control circuit to stop outputting the first control signal to the first positive liquid crystal and the second positive liquid crystal; and
control the second liquid crystal control circuit to output a darkness gradient control signal to the negative-phase liquid crystal for gradually changing a light-shielding number of the auto darkening filter from high to low.

15. The welding mask assembly according to claim 9, wherein the auto darkening filter further comprises at least one of:
a delay setting unit configured to set a filter delay of the auto darkening filter; or
a sensitivity setting unit configured to set a filter sensitivity of the auto darkening filter,
operably to the main control circuit.

16. The welding mask assembly according to claim 10, wherein the auto darkening filter further comprises at least one of:
a delay setting unit configured to set a filter delay of the auto darkening filter; or
a sensitivity setting unit configured to set a filter sensitivity of the auto darkening filter,
operably to the main control circuit.

17. The welding mask assembly according to claim 9, wherein the first positive liquid crystal and the second positive liquid crystal are positive normal-phase liquid crystals; and the negative-phase liquid crystal is a positive negative-phase liquid crystal.

18. The auto darkening filter according to claim 2, further comprising at least one of:

a delay setting unit configured to set a filter delay of the auto darkening filter; or a sensitivity setting unit configured to set a filter sensitivity of the auto darkening filter, operably to the main control circuit.

\* \* \* \* \*